(12) United States Patent
Holm

(10) Patent No.: US 9,139,808 B2
(45) Date of Patent: Sep. 22, 2015

(54) PROCESSOR UNIT FOR PROCESSING AND CONTROLLING A PREPARATION OF A BLOOD SAMPLE AND A METHOD

(75) Inventor: Niels Erik Holm, Birkerod (DK)

(73) Assignee: Vivostat A/S, Allerod (DK)

( * ) Notice: Subject to any disclaimer, the term of this patent is extended or adjusted under 35 U.S.C. 154(b) by 96 days.

(21) Appl. No.: 13/990,326

(22) PCT Filed: Nov. 22, 2011

(86) PCT No.: PCT/EP2011/070618
§ 371 (c)(1),
(2), (4) Date: May 29, 2013

(87) PCT Pub. No.: WO2012/072442
PCT Pub. Date: Jun. 7, 2012

(65) Prior Publication Data
US 2013/0252229 A1   Sep. 26, 2013

(30) Foreign Application Priority Data
Nov. 29, 2010   (EP) .................................. 10192957

(51) Int. Cl.
| | | |
|---|---|---|
| B04B 3/00 | (2006.01) | |
| G01N 21/00 | (2006.01) | |
| C12M 1/00 | (2006.01) | |
| B04B 5/04 | (2006.01) | |
| B04B 13/00 | (2006.01) | |
| G01N 33/49 | (2006.01) | |

(52) U.S. Cl.
CPC .............. *C12M 47/04* (2013.01); *B04B 5/0442* (2013.01); *B04B 13/00* (2013.01); *G01N 33/491* (2013.01); *B04B 2005/0485* (2013.01)

(58) Field of Classification Search
CPC ...... C12M 47/04; B04B 5/0442; B04B 13/00; B04B 2005/0485; G01N 33/491
USPC ......... 210/745, 85, 86, 94, 97, 143, 739, 782; 422/82.05–82.09, 105–108; 435/2, 3; 436/164, 165; 494/1
See application file for complete search history.

(56) References Cited

U.S. PATENT DOCUMENTS

| | | | |
|---|---|---|---|
| 3,674,198 A * | 7/1972 | Eberle ............................. | 494/7 |
| 6,099,740 A * | 8/2000 | Holm et al. ................... | 210/745 |
| 2007/0085996 A1* | 4/2007 | Mangan et al. ................. | 356/39 |

FOREIGN PATENT DOCUMENTS

| | | |
|---|---|---|
| WO | 9830331 | 7/1998 |
| WO | 9830887 | 7/1998 |

OTHER PUBLICATIONS

PCT International Preliminary Report on Patentability in connection with PCT/EP2011/070618 dated Apr. 12, 2013.

(Continued)

*Primary Examiner* — Paul Hyun
*Assistant Examiner* — Robert Eom
(74) *Attorney, Agent, or Firm* — Cooper & Dunham LLP

(57) ABSTRACT

Processor unit for processing and controlling a preparation of a blood sample placed in a preparation unit arranged in said processor unit comprising a piston placed in a first chamber for containing the blood sample. A part of the processed blood moves from the first chamber to a second chamber. The blood sample is centrifuged into separate layers comprising an outer layer adhering to the inner side of the outer first chamber wall and an inner layer placed opposite the outer layer. That the processor unit further comprises a first unit for emitting an outcome signal through the first chamber and a second unit for detecting after the signal has passed the first chamber an income signal. The piston is moved as a function of the detected income signal of the second unit.

13 Claims, 3 Drawing Sheets

(56) References Cited

OTHER PUBLICATIONS

PCT International Search Report in connection with PCT/EP2011/070618, completed on Jan. 16, 2012 and mailed mailed Jan. 24, 2012.

Written Opinion of the International Searching Authority in connection with PCT/EP2011/070618, completed on Jan. 16, 2012 and mailed Jan. 24, 2012.

* cited by examiner

PROCESSOR UNIT FOR PROCESSING AND CONTROLLING A PREPARATION OF A BLOOD SAMPLE AND A METHOD

CROSS-REFERENCE TO RELATED APPLICATIONS

This application is a §371 national stage of PCT International Application No. PCT/EP2011/070618, filed Nov. 22, 2011, claiming priority of European Patent Application No. 10192957.8, filed Nov. 29, 2010, the entire contents of each of which are hereby incorporated by reference into this application in its entirety.

TECHNICAL FIELD

The present invention relates to a processor unit for processing and controlling a preparation of a blood sample placed in a preparation unit arranged in said processor unit, said preparation unit comprising Several chambers communicating with each other at predetermined steps under the processing of the blood sample,
a piston placed in a first chamber for containing the blood sample,
the first chamber comprises an outer first chamber wall and a bottom wall and a top wall in said first chamber the unprocessed blood sample is arranged,
said piston is moved by first moving means from a first position to a new position different from the first position by said movement the volume of the first chamber is changed, a part of the processed blood moves from the first chamber to a second chamber, said chambers being in fluid connection with each other.

Said processor unit further comprises means for centrifugation the preparation unit, the blood sample is centrifuged into separate layers comprising an outer layer adhering to the inner side of the outer first chamber wall and an inner layer placed opposite the outer layer.

The processor unit further comprises a first unit for emitting an outcome signal and a second unit for detecting an income signal said first moving means is activated/regulated by control means as a function of the detected income signal of the second unit by said activation the movement of the piston is regulated.

The invention also relates to a method for processing a blood sample placed in a preparation unit.

BACKGROUND

EP 0951642, which is incorporated herein by reference, discloses a processor unit. A commercial device with the technical principal described in the patent is known and comprises a processor unit in which a container preparation unit comprising several chambers is placed and in said container a sample of blood from a patient is arranged in order to be centrifuged. The process separates the blood into several layers in the first chamber during a centrifugation of the blood sample. The separated layers comprise at least a layer of red blood cells and a layer of plasma.

The plasma is transferred from the first chamber to the second by the movement of a piston that presses the layer of plasma through an opening into a channel that communicates with a second chamber. From the second chamber the plasma is further processed and treated in several chambers before the final product, a fibrin product or a Platelet Rich Fibrin (PRF) product, is extracted and applied in different ways i.e. in order to help the healing of a wound or stop bleeding during the operation of the patient.

The very important part of this process is to secure that the plasma is not contaminated with red blood cells. If this happens, it is due to the fact that red blood cells are transferred into chamber two from chamber one. In order to avoid this, a laser source is placed at the top wall of the container/preparation unit and is sending a signal through the channel that connects chamber one with chamber two. When the absorption of the laser light is changed, the transfer of the substance from chamber one to chamber two is stopped immediately, as this is a sign of red blood cells from the outer layer is contaminating the transferred plasma. Therefore, in this known device, there is a risk that the final product is contaminated with said red blood cells. Further, this way of controlling the process has the draw back that the volume of the transferred plasma is quite small compared to the amount of blood—120 ml—that is treated. Finally the amount of platelets is quite small when the product is used as a PRF product.

WO 98/30331 discloses a processor unit as described above. The movement of the piston of this processor unit is however regulated and controlled by a laser signal emitted from a source, said laser signal hits the surface of the piston. The laser signal is then reflected. The intensity of the reflected signal is registered and a control means stops the movement of the piston rod when a certain value is obtained. The system does not allow the piston to stop and move several times and as a consequence of that, the volume of the transferred plasma obtained by this arrangement is too small and thereby not satisfying.

DISCLOSURE OF THE INVENTION

It is an object of the invention to obtain a new processor unit overcoming at least one of the disadvantages of the prior art or at least providing a useful alternative.

According to a first aspect of the invention, a processor unit as described in the introduction is provided, wherein the processor unit further comprises that the second unit detects the income signal after the outcome signal has passed through the first chamber, said signal emitted through the first chamber is adapted to run parallel with the longitudinal direction of the layers The blood is filled in the preparation unit which is placed in the processor unit. A sample of 120 ml is appropriate. Afterwards the processor unit centrifuges the blood in a certain time and at a velocity of 5-6000 rpm. in the first chamber. The velocity depends on whether the final product should be a fibrin product or a PRF product. During the rotation the blood is separated into at least two layers: a layer of red blood cells adhering to the inner side of the first chamber wall and a layer of plasma placed most far away. In between there might be a layer of platelets; this layer normally arises during the use of the known processor units as described above, but it will be minimized or completely absent during this process due to a faster transfer of the plasma layer from the first chamber to the second chamber.

The first unit sends a signal—advantageously a light signal—which will pass through the layers and parallel with the layers and parallel with the longitudinal axis of the chamber and the piston rod. The income signal that is advantageously the income light signal will be registered and the absorption of light determinates whether the piston should be moved from a start/first position to a new position. The absorption is a function of the thickness of the layers: the thicker red blood cells layer the thinner is the plasma layer and the larger is the absorption of the signal whereby the income signal is reduced.

By this measurement and subsequent movement of the piston the plasma is transferred to the second chamber and the piston will continue to move until the signal has reached a certain (lower) value telling that the amount of plasma is too small and the risk for contaminating the plasma in the second chamber with red blood cells is too high.

The centrifugation continues by which the blood continues to separate into red blood cells and plasma and the piston will be moved again pressing more plasma from the first chamber to the second chamber when the income signal is above the lower value. This continues until the signal of the income signal again has reached a certain value by which the piston stops again and the transfer from the first chamber to the second chamber stops.

By this—in steps—continuous transfer of plasma from the first chamber to the second chamber, the amount of plasma is significantly increased compared to prior art because the transfer of the plasma is started at an earlier stage. Further, the platelets will not separate into a separate layer between the red blood cells and the plasma, but will still be in the plasma solution when the plasma is transferred away from the first chamber. Hereby the amount of platelets is significantly increased in the final processed product, which is an advantage when the product is used for PRF products. The further processing of the plasma takes place as it is described in EP 0951642 which is incorporated by reference.

In a second embodiment of the invention, the first and the second chamber are in fluid communication with each other by a first channel.

In a further embodiment of the invention, a first opening of the first channel is placed near to a centre axis of the first chamber, or near to the outer surface of a piston rod, and the substance of the inner layer is pressed through said first opening and the channel and into the second chamber by the movement of the piston.

This placement of the channel is found to be advantageous as the risk of pressing substances from the outer layer is reduced.

In a further embodiment of the invention, the distance d1 between the first position of the piston and the top wall is larger compared to the distance d2 between the new position and the top wall, and a first channel is placed with a first opening in the top wall and communicating with the first chamber.

In this way the plasma is pressed out from the first chamber into the second chamber and through the channel.

In a further embodiment, the first unit is placed in relation to the first chamber in such a way that the outcome signal of the first unit is running through the bottom and top wall and through the separate layers in the direction from the bottom wall to the top wall. In this way the signal is running parallel with the longitudinal direction of the parallel and separate layers and the centre axis of the piston rod. The red blood cells will absorb more of the signal the broader this layer is.

In an advantageous embodiment, the first unit comprises a light source/emitter that emits the outcome signal, said outcome signal is transferred through the first chamber and being a light signal in the range of 300-1200 nm, moreover in the range 400-800 nm.

Using a light for detecting the amount or width of the plasma layer is a simple way of achieving a suitable signal. Further, such a signal does not interfere with the processing as such of the blood sample. Preferable a LED light (Light Emitting Diode) is chosen, as this does not produce any significant heat and spreads the light. Hereby it is achieved that the whole bottom of the first chamber is radiated.

In a further embodiment the second unit comprises a sensor for detecting the income signal.

The signal is preferable a light signal.

In a further embodiment, the control means comprises a processor. Said processor comprises calculating means for comparing the income signal IS1 with a predetermined value IS. Said control means is designed to activate the first means when IS1 is larger than IS.

Hereby it is controlled that the piston movement stops when the layer of plasma—that is the inner layer—is too narrow and the outer layer—that is the layer of red blood cells—is too wide. By these dimensions the risk for pressing red blood cells into the second chamber and hereby contaminate the plasma in the second chamber is too high.

However, dependent on the algorithm, the comparison between the values could be changed so the control means is activated instead when IS1 is smaller than IS; this is just a question of how the algorithm is defining when to activate the piston. It does not change the fact that the movement of the piston is dependent on the absorption of the signal.

In a further embodiment, the new position comprises at least 3 different positions i.e.
- a second position wherein the centrifugation takes place in a range of 3000-7000 preferable 5000-6000 rpm when the piston moves from the first position up to and including the second position.
- a third position wherein the centrifugation takes place in a range of 3000-7000 preferable 5000-6000 rpm when the piston moves from the second position up to and including the fourth position.
- a fourth position wherein the centrifugation takes place in a range of 3000-7000 preferable 5000-6000 rpm when the piston moves from the third position up to and including the fourth position.

Hereby a suitable velocity for transferring the plasma from the first chamber to the second chamber is achieved simultaneously with the risk of contaminating the plasma with red blood cells is minimized/excluded.

In a further embodiment, the second position is reached when the signal IS1 is equal to or smaller than IS.

In a further embodiment, the third position is reached when the signal IS1 is equal to or smaller than IS.

In a further embodiment, the fourth position is reached when the signal IS1 is equal to or smaller than IS.

By such a continuous transfer of the plasma between the steps/positions, the amount of transferred plasma is optimized. The piston is moved when the signal IS1 is larger than IS.

In a further embodiment, the second layer adheres to a rod of the piston.

In a further embodiment, the second unit for receiving the income signal comprises a light guide. Said light guide is guiding the signal transferred through the first chamber from said chamber to the receiving sensor.

Hereby the background noise is reduced by which the signal value and the validity of the signal are optimized.

In a further embodiment, the second unit for receiving the income signal comprises a photodiode that works in the range 200 nm to 1300 nm, preferably in the range 400 nm to 1100 nm.

In a further embodiment, the second chamber comprises a further component, said component being an enzyme. Said enzyme interacts with the plasma in said chamber The enzyme sees to that the fibrin is extracted. The way the chamber is handling the substance in the chamber is described in EP0951642 which description is incorporated herein by reference.

In a further embodiment, the outer layer comprises a layer of red blood cells.

In a further embodiment, the inner layer comprises a layer of plasma substance.

In a further embodiment, the bottom wall of the first chamber comprises the piston.

In a further embodiment, the outcome signal passes through the bottom of the first chamber.

The invention further relates to a method for processing a blood sample placed in a preparation unit arranged in a processor unit as described above and where the blood sample is placed in the first chamber, an outcome signal is transmitted through the first chamber and parallel with the longitudinal direction of the layers and the income signal is detected by the second unit by which signal the moving means sees to that the piston is moved and continuous to move from a first position to a new position as long as the income signal IS1 has not reached a certain value IS and during said movement of the piston the preparation unit continues to be centrifuged, said movement stops when the value of IS1 equals the value of IS, said movement resumes when the IS1 value again has reached a level above the IS value.

BRIEF DESCRIPTION OF THE DRAWINGS

The invention is explained in details below with reference to the drawings, in which.

DETAILED DESCRIPTION OF THE INVENTION

Figure 1:
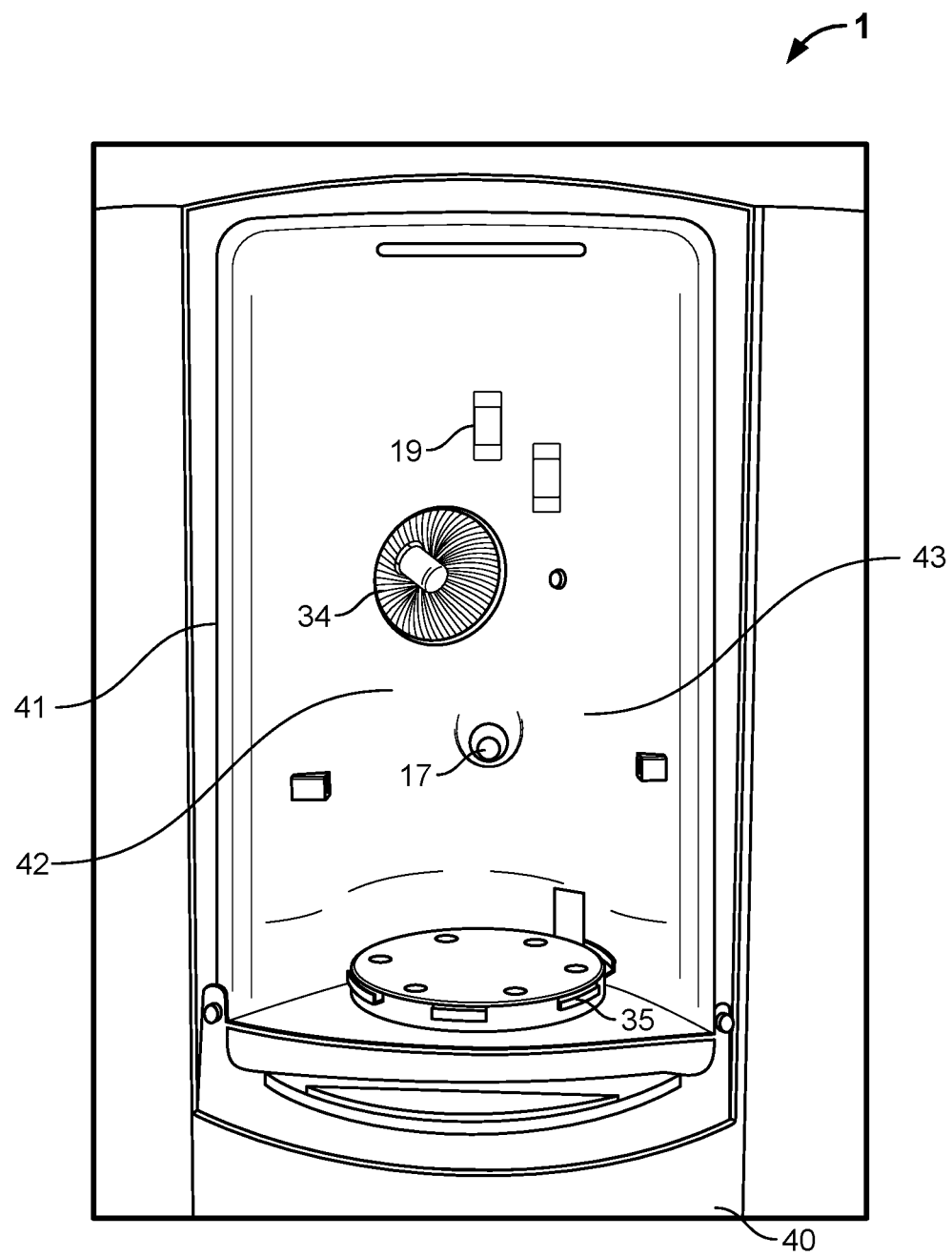
FIG. 1 shows a perspective view of a processor unit according to the invention.

FIG. 1 shows a perspective view of a processor unit 1 according to the invention comprising a housing 40 with an opening 41 into a chamber 42 for placement of a preparation unit 3 (not shown). The preparation unit 3 is placed at and fastened to a supporting turnable 35. This supporting turnable 35 is driven by means for centrifugation of the preparation unit 3 and comprises a device such as a spinel motor. At the back wall 43 of the chamber 42 a first unit 17 such as at least one LED (Light Emitting Diode) is placed i.e. a LUXEON (R I cirkel) of Philips. The LED is arranged in relation to the preparation unit 3 in such a way that the emitted light from the LED is radiating the whole bottom of a first chamber 5 (not shown) of the preparation unit 3 as explained below. Above the first unit 17 a second unit 19 is placed with the purpose of detecting an income signal. Said income signal is measured as the outcome signal from the LED minus the part of the signal that is absorbed in the first chamber 5. The second unit 19 could be a receiver such as at least one sensor, i.e. a Silizium.PIN-Photodiode of Osram. Between the first unit 17 and the second unit 19 a device 34 for heating the bloods to a temperature of 36° C. is placed. This device could advantageously be a lamp which is switched off when the right temperature has been reached.

Figure 2:
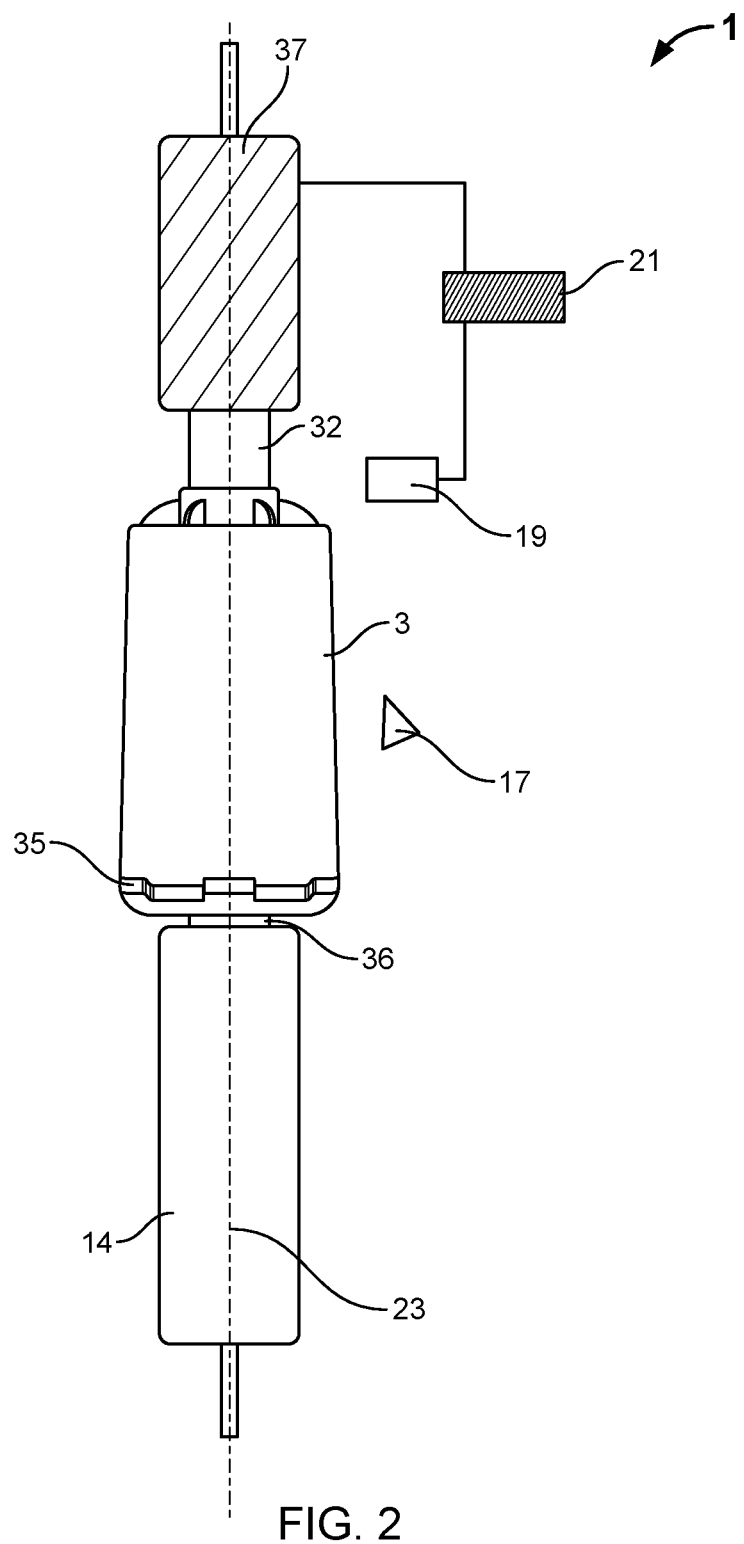
FIG. 2 shows a schematic view of a preparation unit and its relation to different parts of the processor unit according to the invention.

FIG. 2 shows a schematic view of the preparation unit 3 and its relation to different parts of the processor unit 1. The preparation unit 3 is placed at the supporting turnable 35 and is secured to this by gripping means. This supporting turnable 35 is connected to a driving shaft 36 that is further connected to the means for centrifuging the preparation unit 14, i.e. a spinel motor. Opposite this arrangement, a rod of a piston 32 is connected in one end to a piston 4 (not shown) placed in the first chamber 5 of the preparation unit 3. The longitudinal axis of the piston rod 32 is coaxial with the centre axis 23 of the preparation unit 3. The piston rod 32 is at the end placed opposite the piston 4 connected to a motor 37 for driving the piston 4 in the longitudinal direction—that is a sliding movement—in the first chamber 5 (not shown). Outside the preparation unit 3 the first unit 17 is placed near the top of the preparation unit 3 and a little above, the second unit 19 is placed. The second unit 19 is connected to a control means 21 i.e. a processor. Further, the control means 21 is connected to the motor 37. The control means 21 is beforehand programmed with a predetermined value IS and when an income signal IS1, IS2 or IS3 received in the second unit 19 is registered and transferred to the controller 21, the controller 21 compares this signal with the predetermined value IS. Is the signal IS1, IS2 or IS3 below or equal to the value or the predetermined value IS, the processor 21 is programmed to stop the motor 37 and thereby stop the movement of the piston 4. Hereby a transfer of plasma from the first chamber to another chamber in the preparation unit 3 is stopped. This will be explained below. However, the centrifugation of the preparation unit 3 continues as this centrifugation is managed by another control unit and in principle as described in EP0951642.

Figure 3:
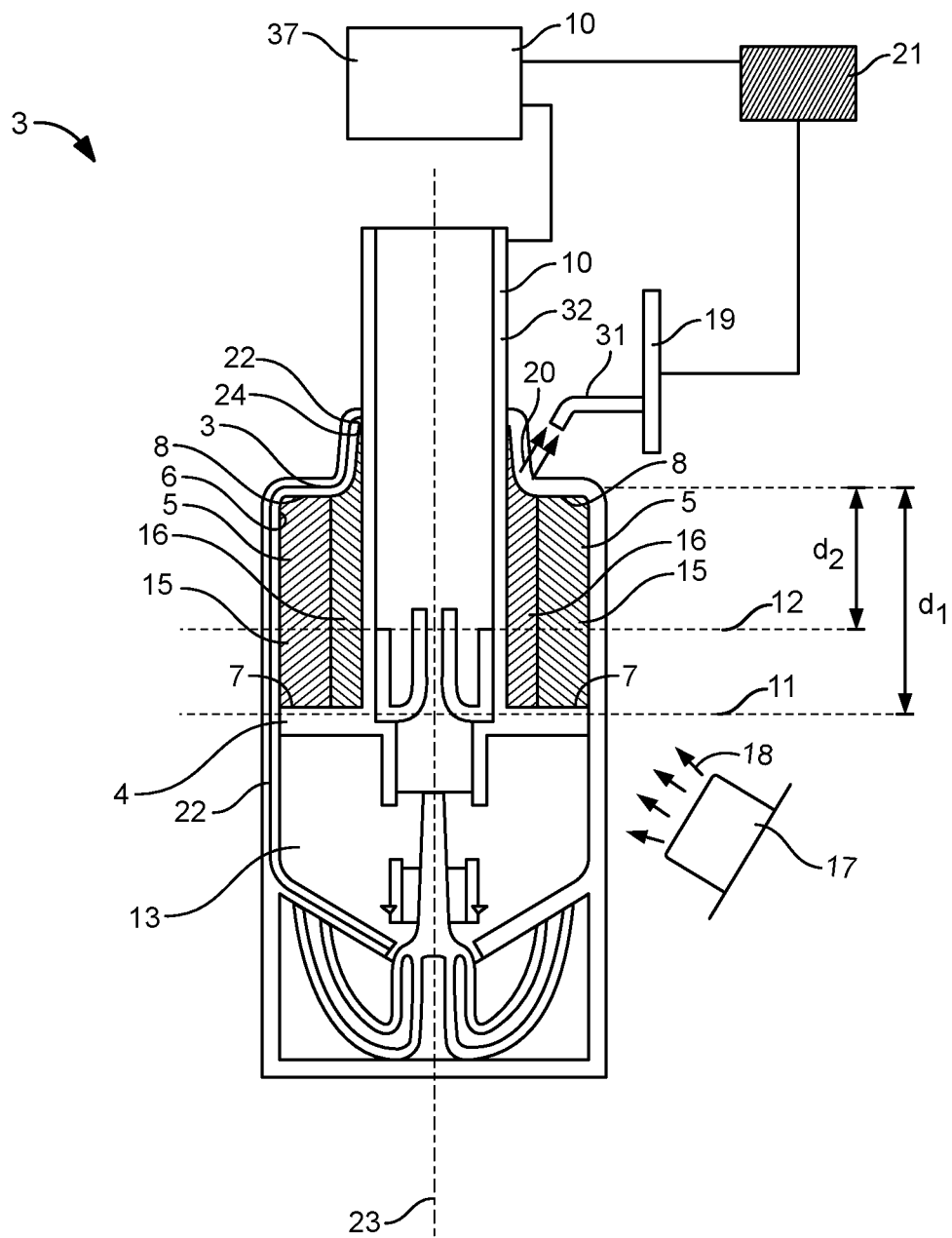
FIG. 3 shows a cross section of a preparation unit and the relation to the first and the second unit in accordance with one embodiment of the invention.

Turning to FIG. 3, this shows a cross sectional view of a preparation unit 3. The preparation unit 3 comprises a cylindrical wall enclosing several chambers and the piston 4. Said preparation unit 3 formed as a container unit and as described in EP0951642. The first moving means 10 comprises the piston rod 32 connected to the motor 37 and the piston 4 placed in the opposite end of the piston rod 32. The piston 4 moves in the longitudinal direction of the preparation unit from a first position 11 to a new position 12 by movement of the piston rod 32. The piston rod 10 is placed in the first chamber 5 of the preparation unit 3. The first chamber 5 comprises and outer cylindrical first chamber wall 6 connected to a top wall 8. A bottom wall 7 is placed opposite the top wall 8. Said walls are embracing the first chamber 5. This bottom wall 7 of the first chamber 5 consists of the piston 4. The piston 4 is a circular plate made in a material that ensures that a signal from the first unit 17 can pass through. The piston 4 is advantageously made of a plastic material such as a polycarbonat material. This material is advantageously also used for the rest of the preparation unit 3. Between the rim of the piston 4 and the outer first chamber wall 6 an O-ring is placed (not shown) whereby the first chamber 5 is leak proof in relation to the chambers placed below. By movement of the piston rod 32 the bottom wall 7/piston 4 is moved from the first position 11 to the new position 12. By said movement the distance d1 between the bottom wall 7 and the top wall 8 in the first position 11 is larger than the distance d2 between the bottom wall 7 and the top wall 8 in the new position 12. By movement of the piston rods 32 and thereby the piston 4 the volume of the first chamber 5 is reduced. The first chamber 5 is in fluid connection via a channel 22 with a second chamber 13 placed below the piston 4 and as described in EP0951642. When the piston is moved to its new position the substance/fluid nearest the piston rods 32 is pressed into the second chamber 13 as a first opening 24 of the channel 22 is placed in the top wall 8 and as near as possible to the piston rod 32.

The first unit 17 is placed outside the preparation unit 3. The first unit 17 is advantageously a light emitter such as a LED. The light signals 18 are emitted to the preparation unit 3 and hit the bottom wall 7 at the side facing towards the second chamber 13. The LED is arranged so the whole surface of the bottom 7 is radiated by the outcome signals 18. The bottom 7/the piston 4 are made in a material that secures that the signals can pass through the wall and into the interior of the first chamber 5. The material is light transmissive in the wave length range of the LED/optical transmitter 17 used. The light signals are running through the first chamber 5 and the signals that are the income signals 20 are leaving through the top wall 8. The top wall 8 is made in the same material as the bottom wall 7 so the signals can be transmitted through the wall. The second unit 19 the sensor receives the income signal 20. The sensor may have a light guide 31 connected in such a way that the income signals 20 are transferred through the light guide 31 to the receiver 19. In this way the risk for background noise is reduced and thereby, the risk for fault signal is also reduced. The light guide 31 could advantageously be formed in a plastic material. From the sensor 19 a signal is sent to the control means 21 and said control means 21 manage the movement of the first moving means 10 as described above. The preparation unit 3 is primary suitable for separation of a component such as Fibrin monomer from blood.

The use of the processor unit 1 and the preparation unit 3 is as follows: When the container/preparation unit 3 is ready for use, a blood sample—approximately 120 ml.—is fed into the first chamber 5 through a needle (not shown). Said blood sample preferably being admixed an anticoagulant and in a conventional manner. During the feeding of the blood into the first chamber 5, air is removed from the first chamber in a conventional manner. After the feeding of the blood, the opening for feeding this blood into the chamber is sealingly closed. Subsequently, the preparation unit 3 with the blood is placed in the processor unit 1. The centrifuge apparatus causes the preparation unit 3 to rotate about the axis of rotation 23. As a result of this centrifuging the blood is separated in the first chamber 5 into a plasma fraction setting radial by inside the remaining portion of the blood and providing the inner layer 16 of the substances. This adheres to the surface of the piston rod 32. The remaining portion containing the red and the white blood cells is placed as an outer layer 15 and closest to the outer first chamber wall 6. Platelets can be present in either fraction as desired by varying the speed and time of centrifugation. In this case the platelets will primarily be in the plasma portion. The rotation speed is in the area of 5000 to 6000 rpm. During the rotation of the preparation unit 3 the first unit 17 is sending outcome signals hitting the bottom 7 of the first chamber 5. Said signals are sent and managed as described above and handled by the second unit 19. The piston 4 would have at least three different positions and all different from the first position 11. The piston 4 will be activated to move towards the top wall 8 when the income signal IS1 is larger than a predetermined value IS. This movement of the piston occurs when the blood has separated into the inner layer 16 being plasma and the outer layer 15 being red blood cells and the inner layer has reached a certain thickness. By movement of the piston 4 the plasma 16 is transferred from the first chamber 5 to the second chamber 13. The centrifugation continues some minutes and during a continuous movement of the piston as long as the value of IS1 exceeds the predetermined value IS. This indicates that only plasma is transferred to the second chamber through the first channel 22. The piston 4 stops as the IS1 falls below IS and will be moved again as soon as sufficient plasma is generated by the centrifugation process by which the thickness of the inner layer 17 is increased. The signal is running parallel with the longitudinal axis or the piston rods 32 and longitudinal with the longitudinal axis of the inner and outer layer 16, 15.

Afterwards, the plasma fraction in chamber 13 is processed as described in EP0951642.

The present invention provides an apparatus and a method for separating blood from a patient into at least two layers and where the volume of the plasma part is significantly increased compared to known technology and known processes. The invention has been described with reference to a specific embodiment but many modifications of the sensors, transmitting devices, material and other components could be carried out without deviating from the scope of the invention and as defined in the claims.

LIST OF REFERENCES

1. Processor unit
2. A blood sample
3. preparation unit
4. A piston
5. First chamber
6. outer first chamber wall
7. bottom wall
8. top wall
9. receiving means
10. first moving means
11. first position
12. new position
13. second chamber
14. means for centrifugation the preparation unit
15. outer layer
16. an inner layer
17. a first unit
18. outcome signal
19. second unit
20. an income signal
21. control means
22. first channel
23. Centre axis first chamber
24. a first opening
25. distance d1
26. distance d2
27. a light source/transmitter
28. a sensor for detecting the income signal
29. a processor
30. calculating means
31. light guide
32. a rod of the piston
33. a photodiode
34. Device for warming blood
35. supporting turnable
36 driving shaft
37 motor for driving the piston
40 housing
41 opening
42 chamber
43 back wall

The invention claimed is:

1. A processor unit for processing and controlling a preparation of a blood sample, said processor unit comprising a preparation unit, the blood sample being placed in said processor unit, said preparation unit comprising several chambers communicating with each other at predetermined steps under the processing of the blood sample, a piston placed in a first chamber for containing the blood sample, the first chamber comprising a cylindrical wall—an outer first chamber wall—a bottom wall comprising a surface of the piston, and a top wall, said walls embracing the first chamber, wherein the unprocessed blood sample is arranged in said first chamber, and said piston is adapted to be moved coaxially with a centre axis of the preparation unit by first moving means from a first position to a new position different from the first position, a volume of the first chamber being reduced by said first moving means whereby a part of the processed blood moves from the first chamber to a second chamber placed below the bottom wall of the first chamber, said chambers being in fluid connection with each other, said first moving means comprising a piston rod connected to a motor and the piston placed at the opposite end of the piston rod, said processor unit further including a spinel motor for centrifugation and rotating the preparation unit around an axis of rotation, whereby the blood sample is centrifuged into separate layers comprising an outer layer adhering to an inner side of the outer first chamber wall and an inner layer placed opposite the outer layer, said layers having a longitudinal direction, the processor unit further comprising a first unit being a light source/transmitter for emitting an outcome light signal and a second unit being a sensor for detecting an income light signal said first moving means is adapted to be activated/regulated by control means comprising a processor as a function of the income light signal of the second unit by said activation the movement of the piston is regulated, characterized in that the second unit detects the income light signal, said outcome light signal being emitted through the bottom wall of the first chamber, through the first chamber, and running parallel with the longitudinal direction of the layers.

2. A processor unit according to claim 1 characterised in that the first and the second chamber are in fluid communication with each other by a first channel.

3. A processor unit according to claim 2 characterised in that a first opening of the first channel is placed near to a centre axis of the first chamber or near an outer surface of the piston rod; and material of the inner layer is pressed through said first opening, through the first channel, and into the second chamber by the movement of the piston.

4. A processor unit according to claim 1 characterised in that a distance between the first position of the piston and the top wall is larger compared to a distance between the new position and the top wall and that a first channel is placed with a first opening in the top wall and communicating with the first chamber.

5. A processor unit according to claim 1 characterised in that the first unit is placed in relation to the first chamber in such a way that the outcome light signal of the first unit is running through the bottom and top wall and through the separate layers in the direction from the bottom wall to the top wall.

6. A processor unit according to claim 1 characterised in that the outcome light signal is transmitted through the first chamber and being in the range of 300-1200 nm.

7. A processor unit according to claim 1 characterised in that the control means is configured to compare the income light signal with a predetermined value and to activate the first moving means when the income light signal is larger than the predetermined value.

8. A processor unit according to claim 1 characterised in that said new position comprises at least 3 different positions, said at least 3 different positions including a second position and wherein the centrifugation takes place in a range of 3000-7000 rpm when the piston moves from the first position up to and including the second position, a third position and wherein the centrifugation takes place in a range of 3000-7000 when the piston moves from the second position up to and including the third position, and a fourth position and wherein the centrifugation takes place in a range of 3000-7000 when the piston moves from the third position up to and including the fourth position.

9. A processor unit according to claim 8 characterised in that the second position is reached when the income light signal is equal to or smaller than a predetermined value.

10. A processor unit according to claim 8 characterised in that the third position is reached when the income light signal is equal to or smaller than a predetermined value.

11. A processor unit according to claim 8 characterised in that the fourth position is reached when the income light signal is equal to or smaller than a predetermined value.

12. A processor unit according to claim 1 characterised in that the second unit further comprises a light guide, wherein the light guide is configured to guide the outcome light signal to the sensor.

13. A processor unit according to claim 1 characterised in that the sensor comprises a photodiode that works in the range 200 nm to 1300 nm.

* * * * *